United States Patent [19]
Karim et al.

[11] Patent Number: 6,156,928
[45] Date of Patent: Dec. 5, 2000

[54] METHOD FOR GAS PHASE PRODUCTION OF ACETIC ACID FROM ETHANE

[75] Inventors: Khalid Karim; M. H. Al-Hazmi; Asad Khan, all of Riyadh, Saudi Arabia

[73] Assignee: Saudi Basic Industries Corporation, Saudi Arabia

[21] Appl. No.: 09/499,809

[22] Filed: Feb. 8, 2000

Related U.S. Application Data

[62] Division of application No. 09/107,115, Jun. 29, 1998.

[51] Int. Cl.⁷ .............................. C07C 51/16; C07C 53/10
[52] U.S. Cl. ............................................ 562/548; 562/607
[58] Field of Search ..................................... 562/548, 607

[56] References Cited

U.S. PATENT DOCUMENTS

| | | | |
|---|---|---|---|
| 3,057,915 | 10/1962 | Riemenschneider et al. | 260/533 |
| 3,131,223 | 4/1964 | Smidt et al. . | |
| 3,240,805 | 3/1966 | Naglieri | 260/533 |
| 3,301,905 | 1/1967 | Riemenschneider et al. | 260/597 |
| 3,907,833 | 9/1975 | Slinkard et al. | 549/258 |
| 4,126,580 | 11/1978 | Lauder | 502/303 |
| 4,146,734 | 3/1979 | Slinkard et al. | 502/304 |
| 4,148,757 | 4/1979 | Brazdil et al. | 252/432 |
| 4,223,161 | 9/1980 | Shaw et al. | 562/534 |
| 4,250,346 | 2/1981 | Young et al. | 585/658 |
| 4,339,355 | 7/1982 | Decker et al. | 252/464 |
| 4,524,236 | 6/1985 | McCain | 585/658 |
| 4,568,790 | 2/1986 | McCain | 585/658 |
| 4,596,787 | 6/1986 | Manyik et al. | 502/312 |
| 4,899,003 | 2/1990 | Manyik et al. | 585/313 |
| 5,049,692 | 9/1991 | Hatano et al. | 558/319 |
| 5,162,578 | 11/1992 | McCain, Jr. et al. | 562/512.2 |
| 5,198,580 | 3/1993 | Bartek et al. | 562/542 |
| 5,300,682 | 4/1994 | Blum et al. | 562/512.2 |
| 6,028,221 | 2/2000 | Karim et al. . | |
| 6,060,421 | 5/2000 | Karim et al. . | |

FOREIGN PATENT DOCUMENTS

| | | | |
|---|---|---|---|
| 0 294 845 | 12/1988 | European Pat. Off. | 88/50 |
| 0 407 091 | 1/1991 | European Pat. Off. . | |
| 0 480 594 | 4/1992 | European Pat. Off. . | |
| 0 518 548 | 12/1992 | European Pat. Off. . | |
| 0 620 205 | 10/1994 | European Pat. Off. | 94/42 |
| 0 627 401 | 12/1994 | European Pat. Off. . | |
| WO 98/05619 | 2/1998 | WIPO . | |

OTHER PUBLICATIONS

E.M. Thorsteinson et al. "The Oxidative Dehydrogenation of Ethane . . . " *Journal of Catalysis* vol. 52, pp. 116–132 (1978).

*Primary Examiner*—James O. Wilson
*Assistant Examiner*—Robert W. Deemie
*Attorney, Agent, or Firm*—William J. Spatz; John E. Boyd

[57] ABSTRACT

A mixed metal oxide catalytic system consisting of molybdenum, vanadium, lanthanum and palladium providing higher yields of acetic acid in low temperature single stage oxidation of ethane with molecular oxygen-containing gas without or with reduced production of by-products such as ethylene and CO.

28 Claims, No Drawings

METHOD FOR GAS PHASE PRODUCTION OF ACETIC ACID FROM ETHANE

RELATED APPLICATIONS

This application is related to U.S. application Ser. No. 08/997,913 (Attorney Docket No.: KR80574-80 (formerly 582815-2080)) filed Dec. 24, 1997, and U.S. application Ser. No. 09/107,046 (Attorney Docket No.: KR 80576-50) filed concurrently herewith, by Karim et al., entitled "Catalyst Systems for the One Step Gas Phase Production of Acetic Acid from Ethylene, Processes of Making and Using the Same", herein incorporated by reference.

BACKGROUND OF THE INVENTION

1. Field of the Invention

This invention relates to a catalyst, a method of making the same and catalytic processes for using the same, more specifically to low temperature selective oxidative dehydrogenation of ethane (or mixture of ethane and ethylene) to acetic acid. The invention also relates to single stage catalytic processes using the novel catalyst featuring increased ethane conversions and acetic acid yields at particular process conditions wherein the product stream does not contain significant amounts of side products such as ethylene and CO.

2. Description of the Related Art

Several publications are referenced in this application. These references describe the state of the art to which this invention pertains, and are incorporated herein by reference.

Due to environmental law constraints, carbon monoxide is an undesirable by-product from an industrial point of view. Furthermore, the separation of ethylene from ethane has a great impact on the process economics of ethane oxidative dehydrogenation processes, where the desired product is an oxygenated hydrocarbon, such as acetic acid.

Acetic acid is conventionally produced by methanol carboxylation using expensive rhodium catalysts in liquid phase homogeneous reactions, which require complicated procedures for the recovery of the catalyst and isolation of the products. More recently, very expensive raw materials for converting ethylene to acetic acid with the production of acetaldehyde as a by-product has been reported.

European Patent Publication EP 02 94 845 discloses a process for the higher selective production of acetic acid by the oxidation of ethane with oxygen in contact with a physical mixture of two catalysts consisting of (A) a catalyst for oxydehydrogenation of ethane to ethylene and (B) a catalyst for hydration/oxidation of ethylene. The ethane oxydehydrogenation catalyst is represented by the formula $Mo_xV_yZ_z$, wherein Z can be one or more of the metals Nb, Sb, Ta, Ca, Sr, Ti, W, Li, Na, Be, Mg, Zn, Cd, Hg, Sc, Fe and Ni. The catalyst for the hydration/oxidation of ethylene is selected from a molecular sieve catalyst, a palladium-containing oxide catalyst, tungsten-phosphorus oxides, or tin molybdenum containing oxide catalysts. European Patent Publication EP 02 94 845 employs the catalyst system prepared by a physical mixture of the two types of catalysts.

The use of molybdenum and vanadium containing catalyst systems for low temperature oxydehydrogenation of ethane to ethylene was reported by E. M. Thorsteinson et al., *Journal of Catalysts*, vol. 52, pp. 116–132 (1978). This paper discloses mixed oxide catalysts containing molybdenum and vanadium together with another transition metal oxide, such as Ti, Cr, Mn, Fe, Co, Ni, Nb, Ta, or Ce. The catalysts are active at temperatures as low as 200° C. for the oxydehydrogenation of ethane to ethylene. Some acetic acid is produced as a by-product.

Several U.S. Pat. Nos. (4,250,346, 4,524,236, 4,568,790, 4,596,787 and 4,899,003) have been granted on low temperature oxydehydrogenation of ethane to ethylene. U.S. Pat. No. 4,250,346 relates to the use of catalysts of the formula $Mo_hV_iNb_jA_k$ in which A is Ce, K, P, Ni, and/or U, h is 16, i is 1 to 8, j is 0.2 to 10, and k is 0.1 to 5. U.S. Pat. No. 4,454,236 is directed to the use of a calcined catalyst of the formula $Mo_aV_bNb_cSb_dX_e$.

The above-cited patents make reference to other patents concerned with the production of ethylene from ethane by the oxydehydrogenation process and all make reference to the formation of acetic acid as a by-product.

U.S. Pat. Nos. 4,339,355 and 4,148,757 relate to oxide catalysts containing Mo, Nb, V and a fourth metal selected from Co, Cr, Fe, In, Mn or Y for the oxidation/ammoxidation of unsaturated aliphatic aldehydes to corresponding saturated aliphatic carboxylic acids.

European Patent Publication EP 04 80 594 is directed to the use of an oxide catalyst composition comprising tungsten, vanadium, rhenium and at least one of the alkaline metals for the production of ethylene and acetic acid by oxidation of ethane with a molecular oxygen containing gas. The replacement of tungsten in whole or part by molybdenum carried out in European Patent Publication EP 04 07 091 results in an increase in selectivity to acetic acid at the expense of the selectivity to ethylene.

European Patent Publication EP 05 18 548 relates to a process for the production of acetic acid by ethane oxidation in contact with a solid catalyst having the empirical formula $VP_aM_bO_x$, where M is one or more optional elements selected from Co, Cu, Re, Nb, W and many other elements, excluding molybdenum, a is 0.5 to 3, b is 0 to 0.1.

European Patent Publication EP 06 27 401 relates to the use of a $V_aTi_bO_x$ catalyst for the oxidation of ethane to acetic acid. The catalyst composition may comprise additional components from a large list of possible elements.

Furthermore, catalysts containing MoVNb promoted with phosphorus and boron have recently been reported as producing a relatively higher yield of acetic acid as compared to unpromoted catalysts with the production of by-products such as carbon monoxide, carbon dioxide and ethylene. See, U.S. application Ser. No. 08/932,075, filed Sep. 17, 1997, by Karim et al., entitled "Catalysts for the Oxidation of Ethane to Acetic Acid, Processes of Making Same and Processes of Using the Same".

More recently, a catalyst containing niobium, palladium, molybdenum and vanadium is reported for use in an ethane oxidation process. See, U.S. application Ser. No. 08/997,913, filed Dec. 24, 1997, by Karim et al., entitled "Catalysts For Producing Acetic Acid From Ethane Oxidation, Processes of Making Same And Methods of Using Same". From a commercial point of view, niobium is an expensive raw material which can have a great impact on the catalyst cost and consequently on the process economics.

Thus, none of these publications have disclosed or suggested the advantages of the catalysts disclosed in present invention which are commercially cheaper and have higher performance for selective production of acetic acid through single stage partial oxidation process of ethane with reduced or zero production of carbon monoxide and ethylene and higher yield and/or selectivity of acetic acid.

OBJECTS OF THE INVENTION

It is an object of the invention to overcome the above-identified deficiencies.

It is another object of the invention to provide improved methods of performing fluid phase catalytic chemical reactions.

It is yet another object of the invention to provide improved catalyst systems for the production of acetic acid from ethane.

It is a further object of the invention to provide an improved method of making acetic acid with enhanced selectivity and yield of the desired product, such as acetic acid, and reduced production of by-products such as carbon monoxide.

It is a still further object of the invention to provide methods of making and using the improved catalysts for the production of acetic acid.

The foregoing and other objects and advantages of the invention will be set forth in or apparent from the following description.

SUMMARY OF THE INVENTION

The present invention relates generally to improved fluid phase catalytic reactions and to the improved catalysts for performing such reactions. More specifically, the present invention relates to methods wherein ethane is oxidized with molecular oxygen to acetic acid in a gas phase reaction at relatively high levels of conversion, selectivity and productivity, preferably at temperatures 150° C. to 450° C. and at pressures 1–50 bar. This is achieved by using as a catalyst with a calcined composition of $Mo_aV_bPd_cLa_dO_x$, wherein:

a is 1 to 5;

b is 0.01 to 0.9;

c is 0.0000001 to 0.5;

d is 0.0000001 to 0.2; and x is a number determined by the valence requirements of the other elements in the catalyst composition, preferably between about 5 and 30.

The numerical values of a, b, and c represent the relative gram-atom ratios of the elements Mo, V, La and Pd, respectively, in the catalyst. The elements are believed to be present in combination with oxygen in the form of various oxides.

DETAILED DESCRIPTION OF THE INVENTION

One aspect of the invention relates to the improved Mo-V-Pd-La-O catalyst systems useful in fluid phase catalytic chemical reactions such as the direct conversion of ethane to acetic acid by means of ethane oxidation. Using the novel catalyst, higher yields and/or selectivity to acetic acid are achieved with lower levels of by-products such as carbon monoxide and/or ethylene. According to one preferred embodiment, no measurable amount of carbon monoxide and/or ethylene by-products are produced.

The catalyst of the invention can be used with or without a support. Suitable supports for the catalyst include alumina, silica, titania, zirconia, zeolites, silicon carbide, Mo carbide, molecular sieves and other microporous/nanoporous materials, and mixtures thereof. When the catalyst is used on a support, the supported catalyst preferably comprises from about 5 to 50% by weight of the catalyst composition, and 50 to 95% by weight support material.

Another aspect of the invention relates to methods of making the improved catalysts of the invention having the formula $Mo_{1-5}V_{0.1-0.9}Pd_{0.0000001-0.5}La_{0.0000001-0.2}$. The choice of the precursor compounds used as well as the specific procedures followed in preparing a catalyst can have a significant effect on the performance of a catalyst.

Preferably, the catalyst is prepared from a solution of soluble compounds (salts, complexes or other compounds) of each of the metals. The solution is preferably an aqueous system having a pH of 1 to 10, more preferably a pH of 1 to 7, at a temperature of from about 30° C. to about 100° C.

Generally, a mixture of compounds containing the elements is prepared by dissolving sufficient quantities of soluble compounds and dispersing the insoluble compounds so as to provide the desired gram-atom ratios of the elements in the catalyst composition. The catalyst composition is then prepared by removing the water and/or other solvent from the mixture of the compounds in the solution system. The dried catalyst is calcined by heating to a temperature from about 250° C. to about 450° C. in air or oxygen for a period of time from about one hour to about 16 hours to produce the desired catalyst composition.

Preferably, the molybdenum is introduced into the solution in the form of ammonium salts such as ammonium paramolybdate, or organic acid salts of molybdenum such as acetates, oxalates, mandelates, and glycolates. Some other partially water soluble molybdenum compounds which may be used include molybdenum oxides, molybdic acid, and chlorides of molybdenum.

Preferably, the vanadium is introduced into the solution in the form of ammonium salts such as ammonium metavanadate and ammonium decavanadate, or organic salts of vanadium such as acetates, oxalates, and tartrates. Partially water soluble vanadium compounds such as vanadium oxides and sulfates of vanadium can also be used. To achieve complete solubility, a certain amount of oxalic or tartaric acid can be added. Preferably, the lanthanum is introduced into the catalyst slurry in the form of a salt of La such as oxide, nitrate, etc.

Preferably, the palladium is introduced into catalyst slurry in the form of Pd on activated charcoal or alumina or a solution of salts of palladium such as acetate, chloride, nitrate etc.

Preferably, the catalyst is prepared by the following general procedure. Aqueous solutions of vanadium and molybdenum are prepared separately. The vanadium solution is mixed with the molybdenum solution at a particular temperature preferably ranging from 80 to 90° C. and a pH preferably between 1 and 5. The third component (palladium) is slowly added to the combined gel solution. For supported catalysts, the required amount of suitable support material, mentioned above, can be added to the above combined gel solution.

After mixing and heating for about ½ to 2 hours, the resultant gel is dried to incipient wetness with continuous stirring at about 100° C.

After drying the resultant gel mixture at 120° C. for 16 hours, the catalyst is heated to 350° C. at the rate of 2° C. per minute and calcined at this temperature in air for 4 hours to produce the desired oxide composition. This regime appears to be close to optimum as it provides a catalyst with the desired structure and properties.

Another aspect of the invention relates to methods of using the improved catalyst.

The improved catalyst systems may be used in a variety fluid phase catalytic chemical reactions for converting at least one fluid phase reactant into at least one fluid phase product.

According to one embodiment, the reaction oxidizes lower alkanes to corresponding acids.

According to another embodiment, the fluid phase reactants comprise alpha-beta unsaturated aliphatic aldehydes and an oxygen-containing gas (e.g., air, oxygen, etc.) and the fluid phase products comprise alpha-beta unsaturated carboxylic acids.

Accordingly, the catalyst of the invention is not limited to the oxydehydrogenation of ethane to acetic acid and may be applied for oxidizing alpha-beta unsaturated aliphatic aldehydes in the vapor phase with molecular oxygen to produce the corresponding alpha-beta unsaturated carboxylic acids and $C_3$ alkane or alkene to correspondence acids.

According to a preferred embodiment, the fluid phase reactants comprise ethane and the fluid phase products comprise acetic acid.

The raw material used as the source of the ethane can be a gas stream which contains at least five volume percent of ethane or mixture of ethane and ethylene. The gas stream can also contain minor amounts of the $C_3$–$C_4$ alkane and alkenes, less than five volume percent of each. The gas stream can also contain major amounts, more than five volume percent, of nitrogen, carbon dioxide, and water in the form of steam.

The reaction mixture used in carrying out the process is generally one mole of ethane, 0.01 to 2.0 moles of molecular oxygen either as pure oxygen or in the form of air, and zero to 4.0 moles of water in the form of steam. The water vapor or steam is used as a reaction diluent and as a heat moderator for the reaction and it also acts as a desorption accelerator of the reaction product in the vapor phase oxidation reaction. Other gases may be used as reaction diluents or heat moderators such as helium, nitrogen, and carbon dioxide.

The gaseous components of the reaction mixture may include ethane, oxygen and a diluent, and these components are preferably uniformly admixed prior to being introduced into the reaction zone. The components may be preheated, individually or after being admixed, prior to being introduced into the reaction zone which should have temperature of from about 150° C. to about 450° C.

The oxygen concentration in the feed gas mixture can vary widely, from 0.1 to 50% or higher of the feed mixture by applying proper measures to avoid explosion problems. Air is the preferred source of oxygen in the feed. The amount of oxygen present may be a stoichiometric amount, or lower, of the hydrocarbons in the feed.

The reaction zone generally has a pressure of from 1 to 50 bar, preferably from 1 to 30 bar; a temperature of from about 150° C. to about 450° C., preferably from 200° C. to 300° C.; a contact time between the reaction mixture and the catalyst of from about 0.01 second to 100 seconds, preferably from 0.1 second to 10 seconds; and a space hourly velocity of from about 50 to about 50,000 $h^{-1}$, preferably from 100 to 10,000 $h^{-1}$ and most preferably from 200 to 3,000 $h^1$.

The contact time is defined as the ratio between the apparent volume of the catalyst bed and the volume of the gaseous reaction mixture feed to the catalyst bed under the given reaction conditions in a unit of time.

The space velocity is calculated by determining total reactor outlet gas equivalent in liters of the total effluent evolved over a period of one hour divided by the liters of catalyst in the reactor. This room temperature volume is converted to the volume at 0° C. at 1 bar.

The reaction pressure may be initially provided by the feed of the gaseous reactant and diluent and, after the reaction has commenced, maintained by the use of suitable back-pressure controller placed on the reactor outlet stream.

The reaction temperature is preferably provided by placing the catalyst bed within a tubular converter having walls which is placed in a furnace heated to the desired reaction temperature.

The improved catalysts of the invention provide unexpectedly high yields of acetic acid using a single stage conversion of ethane to acetic acid. This may be achieved using the single catalyst composition of the invention in a single reaction zone.

Preferably, the yield(%) of acetic acid is greater than 15%, more preferably greater than 20%, even more preferably greater than 25% and most preferred greater than 30%.

Surprising, the single stage conversion of ethane to acetic acid provides reduced levels of by-products such as carbon monoxide and ethylene. Preferably, the selectivity (%) to carbon monoxide is less than 2%, more preferably less than 1.5%, even more preferably less than 1%, still further preferred less than 0.5% and most preferred about 0%. Preferably, the yield (%) of ethylene is less than 2%, more preferably less than 1.5%, even more preferably less than it, still further preferred less than 0.5% and most preferred about 0%.

The process is generally carried out in a single stage with all the oxygen and reactants being supplied as a single feed with non-reacted initial reactants being recycled. However, multiple stage addition of oxygen to the reactor with intermediate hydrocarbon feed can also be used. This may improve productivity to acetic acid and avoid potentially hazardous conditions.

EXAMPLES

The following examples are illustrative of some of the products and methods of making the same falling within the scope of the present invention. They are, of course, not to be considered in any way limitative of the invention. Numerous changes and modifications can be made with respect to the invention by one of ordinary skill in the art.

Examples given in Table I were carried out to demonstrate embodiments of the invention.

CATALYST TESTING: Catalyst evaluations were carried out in a stainless steel fixed bed tubular reactor under standard process conditions using an autoclave BTRS Jr reactor. The gas feed composition was 15% by volume ethane and 85% by volume air at a reaction temperature of 260° C., at a pressure of 200 psig and at space velocity of about 1,100 $h^{-1}$ using 3 grams of calcined catalyst.

Reaction products were analyzed on-line by gas chromatography. Oxygen, nitrogen and carbon monoxide were analyzed using a 2.5 m by 3 mm column of 13X molecular sieve. Carbon dioxide, ethane and ethylene were analyzed using a 0.5 m by 3 mm column packed with material sold under the trade name PORAPACK N. Acetic acid and water were analyzed using a 1.5 m by 3 mm column packed with material sold under the trademark HAYASEP Q. In all cases, the conversion and selectivity calculations were based on the reaction stoichiometry:

EXAMPLE 1

$$Mo_1V_{0.628}Pd_{2.88E-04}La_{1E-05}$$

Ammonium metavanadate (Aldrich Chemicals, Assay=99.0%) in the amount of 6 grams was added to 65 ml of distilled water and heated to 80–90° C. with stirring. Six grams of oxalic acid were added to the above solution. The color of the solution changed from yellowish green to dark brown with a pH between 2 and 2.5 at 80° C. (solution A). Ammonium paramolybdate tetrahydrated (Aldrich Chemicals A.C.S -12054-85-2) in the amount of 14.4 grams was added to 16.7 ml of water and heated to 65° C. to give a colorless solution with a pH between 5.0 and 6.5 (solution B). Solution B was mixed slowly with solution A to give dark blue-green color solution with a pH of 4.22 at 91° C. The 2.5E-03 grams of palladium was added slowly to the gel mixture followed by the required amount of lanthanium nitrate. This dark color combination was stirred vigorously to achieve a homogeneous gel mixture which was then dried slowly to incipient dryness within 60 to 120 minutes at 95–98° C. with continuous stirring.

The resulting solid was put in a China dish and dried additionally in an oven at 120° C. for sixteen hours. The dried material was cooled to room temperature and placed in a furnace. The temperature was raised from room temperature to 350° C. at the rate of 2° C./min. and thereafter held at 350° C. for four hours.

Example 8 was prepared to check the reproducibility of the catalytic materials.

EXAMPLE 2

$Mo_1V_{0.398}Pd_{2.88E-04}La_{1.0E-05}$

The procedure was the same as Example 1 except 3.8 grams of ammonium metavanadate (Aldrich Chemicals, Assay=99.0%) were used.

EXAMPLE 3

$Mo_1V_{0.628}Pd_{2.88E-04}La_{1.0E-05}$

The procedure was the same as Example 1 except 4 grams of oxalic acid were used.

EXAMPLE 4

$Mo_1V_{0.628}Pd_{2.88E-04}La_{1.0E-05}$

The procedure was the same as Example 1 except 12 grams of oxalic acid were used.

EXAMPLE 5

$MO_1V_{0.773}Pd_{2.88E-04}La_{1.0E-05}$

The procedure was the same as Example 1 except 7 grams of ammonium metavanadate (Aldrich Chemicals, Assay=99.0%) were used.

EXAMPLE 6

$Mo_1V_{0.584}Pd_{2.67E-04}La_{1.0E-05}$

The procedure was the same as Example 1 except 15.5 grams of ammonium paramolybdate tetra hydrated (Aldrich Chemicals A.C.S -12054-85-2) were used.

EXAMPLE 7

$Mo_1V_{0.628}Pd_{3.45E-04}La_{1.0E-05}$

The procedure was the same as Example 1 except 3.0E-03 grams of palladium were used.

EXAMPLE 8

$Mo_1V_{0.628}Pd_{2.88E-04}La_{1.0E-05}$

The procedure was the same as Example 1 in order to check the reproducibility of the catalyst.

RESULTS

The BET surface area for the catalysts described in examples varies from 25 to 35 m2/g.

Catalyst evaluation data for the above mentioned examples is given in Table II.

TABLE 2

CATALYST EVALUATION DATA
(Reaction conditions: 260° C., 200 psi, Ethane:Air (15%:85%), F/W 10)

| Example No. | Conversion (%) | | Selectivity (%) | | | Yield (%) | |
|---|---|---|---|---|---|---|---|
| | Ethane | Oxygen | Acetic Acid | CO | $CO_2$ | Ethylene | Acetic Acid |
| 1 | 58.24 | 100 | 67.89 | 0 | 32.10 | 0 | 39.53 |
| 2 | 37.75 | 71.23 | 67.45 | 0 | 32.54 | 0 | 25.71 |
| 3 | 37.42 | 67.17 | 65.17 | 0 | 34.93 | 0 | 24.38 |
| 4 | 36.34 | 63.87 | 68.05 | 0.45 | 30.69 | 1.0 | 24.73 |
| 5 | 41.83 | 76.45 | 68.72 | 0 | 31.27 | 0.0 | 28.75 |
| 6 | 26.85 | 50.22 | 71.65 | 0 | 28.35 | 0 | 19.23 |
| 7 | 51.84 | 99.57 | 64.30 | 0 | 35.70 | 0 | 33.36 |
| 8 | 56.65 | 100 | 67.30 | 0 | 32.70 | 0 | 38.12 |

The catalysts of the present invention showed an optimum redox behavior resulting a high activity and highly selective towards the partial oxidation products. Based on the catalytic data, the following general characteristics can be concluded for the catalysts of the present invention.

1. High conversion of ethane reflects a high rate of oxy-dehydrogenation of alkane.

2. High rate of oxygenation of ethylene to acetic acid.

The above description of the invention is intended to be illustrative and not limiting. Various changes or modifications in the embodiments described may occur to those skilled in the art. These can be made without departing from the spirit or scope of the invention.

What is claimed is:

1. A single stage catalytic process for direct conversion of ethane to acetic acid by means of ethane oxidation comprising the step of oxidizing ethane in a reaction mixture comprising ethane and oxygen or a compound capable of providing oxygen in a reaction zone in the presence of a catalyst containing a catalyst composition comprising the elements Mo, V, Pd, and La in the form of oxides, in the following ratio:

$Mo_aV_bPd_cLa_dO_x$ a is 1 to 5;
b is 0.01 to 0.9;
c is 0.0000001 to 0.5; and
d is 0.0000001 to 0.2;

wherein x is a number determined by the valence requirements of the other elements in the catalyst composition.

2. The process of claim 1, wherein said catalyst is in the form of a fixed or fluidized bed and said oxidation is carried out by a feed mixture comprising ethane introduced into said reaction zone.

3. The process of claim 2, wherein said feed mixture further comprises air.

4. The process of claim 2, wherein said feed mixture comprises oxygen.

5. The process of claim 2, wherein said feed mixture comprises molecular oxygen ranging from 0.1 to 50% by volume of the feed mixture.

6. The process of claim 2, wherein said feed mixture is diluted with steam in an amount ranging from 0 to 40% by volume.

7. The process of claim 1, wherein said oxidation is achieved while operating in gas phase at a temperature of from 150 to 450° C., under a pressure of from 1 to 50 bars, and with a contact time between the reaction mixture and the catalyst of from 0.1 to 10 seconds.

8. The process of a claim 1, wherein said oxidation provides 70% selectivity to acetic acid at a 60% conversion of ethane per single pass through said reaction zone.

9. The process of a claim 1, wherein said oxidation of ethane produces no CO and no ethylene as by-products using molecular oxygen with a range from 0.1 to 50% of the feed mixture.

10. The process of claim 1, further comprising the step of introducing oxygen into the feed mixture to increase the yield, selectivity or both yield and selectivity of acetic acid.

11. A process for performing a catalytic chemical reaction in fluid phase comprising at least one reactant in fluid phase under suitable reaction conditions with a catalyst containing a catalyst composition comprising the elements Mo, V, Pd, and La in the form of oxides, in the ratio $$Mo_a V_b Pd_c La_d O_x$$

a is 1 to 5;
b is 0.01 to 0.9;
c is 0.0000001 to 0.5; and
d is 0.0000001 to 0.2;
wherein x is a number determined by the valence requirements of the other elements in the catalyst composition.

12. A process for performing a catalytic chemical reaction comprising the step of introducing a reactant in fluid phase into a reaction zone containing a catalyst having a catalyst composition comprising the elements Mo, V, Pd, and La in the form of oxides, in the ratio $$Mo_a V_b Pd_c La_d O_x$$

a is 1 to 5;
b is 0.01 to 0.9;
c is 0.0000001 to 0.5; and
d is 0.0000001 to 0.2;
wherein x is a number determined by the valence requirements of the other elements in the catalyst composition.

13. The process of claim 11, wherein said catalytic chemical reaction converts one or more fluid phase reactants to one or more fluid phase products.

14. The process of claim 11, wherein said catalytic chemical reaction oxidizes lower alkanes to corresponding acids.

15. The process of claim 13, wherein said one or more fluid phase reactants comprise ethane and said one or more fluid phase products comprise acetic acid.

16. The process of claim 13, wherein said one or more fluid phase reactants comprise alpha-beta unsaturated aliphatic aldehydes and oxygen and said one or more fluid phase products comprise alpha-beta unsaturated carboxylic acids.

17. The process of claim 1, wherein said catalyst composition is made by a method comprising the steps of:
   a) combining the elements Mo, V, Pd, and La in the following ratio:

$$Mo_a V_b Pd_c La_d$$

a is 1 to 5;
b is 0.01 to 0.9;
c is 0.0000001 to 0.5; and
d is 0.0000001 to 0.2,
to form a mixture, and
   b) calcining said mixture to form said catalyst composition.

18. The process of claim 1, wherein selectivity to carbon monoxide is less than 2%.

19. The process of claim 1, wherein said catalyst is a supported catalyst comprising a support.

20. The process of claim 19, wherein the said support is selected from the group consisting of alumina, silica, titania, zirconia, silicon carbide, Mo-carbide, zeolites and molecular sieves and other microporous/nanoporous materials and mixtures thereof.

21. The process of claim 19, wherein said supported catalyst comprises from 5 to 50% by weight catalyst composition and 50 to 95% by weight support.

22. The process of claim 1, wherein said catalyst composition consists essentially of the elements Mo, V, Pd, and La in the form of oxides.

23. The process of claim 1, wherein said catalyst composition is formed by a method comprising the steps of:
   (a) forming a mixture containing Mo, V, Pd, and La in a solution;
   (b) drying said mixture to form a dried solid material; and
   (c) calcining said dried solid material to form said catalyst.

24. The process of claim 23, wherein said mixture is an aqueous system having a pH from 1 to 10.

25. The process of claim 23, wherein said mixture is an aqueous system having a pH from 1 to 7.

26. The process of claim 23, wherein said mixture is formed by combining a first solution with a second solution, wherein said first solution and said second solution each contain at least one element selected from the group consisting of Mo, V, Pd, and La.

27. The process of claim 23, wherein said calcining comprises heating said dried solid material to a calcining temperature from about 250 to 450° C. in air or oxygen for period of time from about one hour to about 16 hours.

28. A single stage catalytic process for direct conversion of ethane to acetic acid by ethane oxidation comprising the step of oxidizing ethane in a reaction mixture comprising ethane and oxygen or a compound capable of providing oxygen in a reaction zone in the presence of a catalyst containing a catalyst composition made by a method comprising the steps of:
   a) combining the elements Mo, V, Pd, and La in the following ratio:

$$Mo_a V_b Pd_c La_d$$

a is 1 to 5;
b is 0.01 to 0.9;
c is 0.0000001 to 0.5; and
d is 0.0000001 to 0.2,
to form a mixture, and
   b) calcining said mixture to form said catalyst composition.

* * * * *